United States Patent
Ainsworth et al.

(10) Patent No.: US 12,155,665 B2
(45) Date of Patent: Nov. 26, 2024

(54) METHODS AND SYSTEM FOR MONITORING AND ASSESSING EMPLOYEE MOODS

(71) Applicant: Sensormatic Electronics, LLC, Boca Raton, FL (US)

(72) Inventors: Peter Alexander Ainsworth, Oxfordshire (GB); Ian C. Westmacott, Tewksbury, MA (US); Martin J. Donaghy, Antrim (GB); Derek Boyes, Armagh (GB); Terry Neill, Antrim (GB); John McKenna, County Derry (GB); Anne Gallagher, Belfast (GB); Mark Paterson, Newtownards Down (GB); Ashish Italiya, Newtownabbey (GB)

(73) Assignee: SENSORMATIC ELECTRONICS, LLC, Boca Raton, FL (US)

( * ) Notice: Subject to any disclaimer, the term of this patent is extended or adjusted under 35 U.S.C. 154(b) by 0 days.

(21) Appl. No.: 16/756,905

(22) PCT Filed: Nov. 2, 2018

(86) PCT No.: PCT/US2018/058984
§ 371 (c)(1),
(2) Date: Apr. 17, 2020

(87) PCT Pub. No.: WO2019/090096
PCT Pub. Date: May 9, 2019

(65) Prior Publication Data
US 2021/0196169 A1 Jul. 1, 2021

Related U.S. Application Data

(60) Provisional application No. 62/581,207, filed on Nov. 3, 2017.

(51) Int. Cl.
*G06Q 10/0631* (2023.01)
*A61B 5/1171* (2016.01)
(Continued)

(52) U.S. Cl.
CPC .......... *H04L 63/102* (2013.01); *A61B 5/1176* (2013.01); *A61B 5/165* (2013.01);
(Continued)

(58) Field of Classification Search
CPC ....... G07C 9/257; A61B 5/1176; A61B 5/165; A61B 2503/24; G06K 9/00771;
(Continued)

(56) References Cited

U.S. PATENT DOCUMENTS 4,777,478 A   10/1988  Hirsch et al.
6,904,168 B1   6/2005  Steinberg et al.
(Continued)

FOREIGN PATENT DOCUMENTS

CN            105516659 A  *  4/2016  ......... G06K 9/00302
DE     10 2009 000 006        7/2010
(Continued)

OTHER PUBLICATIONS

Y. Lutchyn, P. Johns, A. Roseway and M. Czerwinski, "MoodTracker: Monitoring collective emotions in the workplace," 2015 International Conference on Affective Computing and Intelligent Interaction (ACII), 2015, pp. 295-301, doi: 10.1109/ACII.2015.7344586. (Year: 2015).*
(Continued)

*Primary Examiner* — Michael Robert Cammarata
(74) *Attorney, Agent, or Firm* — ArentFox Schiff LLP (57) ABSTRACT

Methods and system for monitoring and assessing employee moods are disclosed. A proposed enterprise employee monitoring system includes surveillance cameras, a facial recognition module, an emotional analyzer module, and an
(Continued)

employee database. The surveillance cameras capture image data including employee individuals within the enterprise. The facial recognition module identifies the individuals in the image data, and the emotional analyzer module determines an emotional state of the individuals based upon the image data. The employee database stores employee information and the emotional state information from the emotional analyzer module, based upon the identification performed by the facial recognition module.

15 Claims, 4 Drawing Sheets

(51) Int. Cl.

| | |
|---|---|
| A61B 5/16 | (2006.01) |
| G06Q 10/105 | (2023.01) |
| G06Q 10/1093 | (2023.01) |
| G06V 40/16 | (2022.01) |
| G07C 9/00 | (2020.01) |
| G07C 9/25 | (2020.01) |
| G07C 9/30 | (2020.01) |
| G07C 9/37 | (2020.01) |
| G08B 13/196 | (2006.01) |
| H04L 9/40 | (2022.01) |
| H04N 7/18 | (2006.01) |
| H04W 4/02 | (2018.01) |
| H04W 4/029 | (2018.01) |
| G06Q 50/26 | (2024.01) |

(52) U.S. Cl.
CPC ....... *G06Q 10/0631* (2013.01); *G06Q 10/105* (2013.01); *G06Q 10/1093* (2013.01); *G06V 40/166* (2022.01); *G06V 40/172* (2022.01); *G07C 9/00904* (2013.01); *G07C 9/257* (2020.01); *G07C 9/30* (2020.01); *G07C 9/37* (2020.01); *G08B 13/19608* (2013.01); *H04L 63/105* (2013.01); *H04N 7/181* (2013.01); *H04W 4/023* (2013.01); *H04W 4/029* (2018.02); *A61B 2503/24* (2013.01); *G06Q 50/26* (2013.01); *G06V 40/16* (2022.01); *G06V 40/174* (2022.01)

(58) Field of Classification Search
CPC ........... G06K 9/00221; G06K 9/00302; G06Q 10/063114; G06Q 10/105; G08B 13/19608; H04L 67/22; H04L 63/102; G06V 20/52; G06V 40/16; G06V 40/172; H04W 4/029
See application file for complete search history.

(56) References Cited

U.S. PATENT DOCUMENTS

| | | | | |
|---|---|---|---|---|
| 7,921,036 | B1* | 4/2011 | Sharma | G06Q 30/02 |
| | | | | 705/14.66 |
| 8,219,438 | B1* | 7/2012 | Moon | G06Q 30/0201 |
| | | | | 705/7.29 |
| 9,711,034 | B2 | 7/2017 | Daniel | |
| 9,858,632 | B1 | 1/2018 | Shipman et al. | |
| 9,996,736 | B2* | 6/2018 | Smith | G06K 9/00771 |
| 10,033,965 | B1 | 7/2018 | Clements et al. | |
| 10,109,171 | B1* | 10/2018 | M A M | G08B 21/02 |
| 10,121,070 | B2 | 11/2018 | Derenne et al. | |
| 10,176,513 | B1* | 1/2019 | Koka | H04N 7/183 |
| 10,716,473 | B2 | 7/2020 | Greiner | |
| 10,732,722 | B1* | 8/2020 | Heraz | G06F 3/017 |
| 10,755,540 | B1 | 8/2020 | Kocher | |
| 11,176,357 | B2 | 11/2021 | Wang et al. | |
| 2002/0083025 | A1* | 6/2002 | Robarts | G06F 21/6245 |
| | | | | 706/12 |
| 2002/0132663 | A1 | 9/2002 | Cumbers | |
| 2002/0191817 | A1 | 12/2002 | Sato et al. | |
| 2003/0210139 | A1 | 11/2003 | Brooks et al. | |
| 2003/0217024 | A1 | 11/2003 | Kocher | |
| 2004/0210159 | A1* | 10/2004 | Kibar | A61B 5/4803 |
| | | | | 600/558 |
| 2004/0234108 | A1 | 11/2004 | Li et al. | |
| 2005/0075116 | A1 | 4/2005 | Laird et al. | |
| 2005/0091338 | A1 | 4/2005 | de la Huerga et al. | |
| 2005/0284200 | A1 | 12/2005 | Moon et al. | |
| 2006/0024020 | A1 | 2/2006 | Badawy | |
| 2006/0149589 | A1 | 7/2006 | Wager | |
| 2006/0190419 | A1* | 8/2006 | Bunn | G06K 9/00771 |
| | | | | 706/2 |
| 2008/0033752 | A1 | 2/2008 | Rodgers | |
| 2008/0091515 | A1* | 4/2008 | Thieberger | G06Q 10/04 |
| | | | | 705/7.11 |
| 2009/0328152 | A1 | 12/2009 | Thomas et al. | |
| 2010/0057592 | A1 | 3/2010 | Moir et al. | |
| 2010/0153146 | A1 | 6/2010 | Angell et al. | |
| 2010/0169134 | A1* | 7/2010 | Cheng | G06Q 10/06 |
| | | | | 705/7.42 |
| 2010/0245536 | A1* | 9/2010 | Huitema | H04N 21/42203 |
| | | | | 348/E7.083 |
| 2011/0091847 | A1* | 4/2011 | Carroll | G09B 19/00 |
| | | | | 434/236 |
| 2011/0134214 | A1 | 6/2011 | Chen et al. | |
| 2011/0134240 | A1 | 6/2011 | Anderson et al. | |
| 2011/0202595 | A1* | 8/2011 | Kakiuchi | H04L 67/54 |
| | | | | 709/203 |
| 2012/0262296 | A1* | 10/2012 | Bezar | G10L 25/63 |
| | | | | 340/573.1 |
| 2013/0012790 | A1* | 1/2013 | Horseman | A61B 5/14551 |
| | | | | 600/301 |
| 2013/0027561 | A1 | 1/2013 | Lee et al. | |
| 2013/0144914 | A1 | 6/2013 | Libal et al. | |
| 2013/0155250 | A1 | 6/2013 | Myers et al. | |
| 2013/0184592 | A1 | 7/2013 | Venetianer et al. | |
| 2014/0018059 | A1 | 1/2014 | Noonan | |
| 2014/0104429 | A1 | 4/2014 | Ward et al. | |
| 2014/0130076 | A1* | 5/2014 | Moore | H04N 21/812 |
| | | | | 725/19 |
| 2014/0139678 | A1 | 5/2014 | Moriarty et al. | |
| 2014/0207950 | A1 | 7/2014 | Badiee et al. | |
| 2014/0210617 | A1 | 7/2014 | Markwitz et al. | |
| 2014/0218164 | A1 | 8/2014 | Mahapatra et al. | |
| 2014/0244264 | A1* | 8/2014 | Thirumalainambi | G10L 25/63 |
| | | | | 704/270 |
| 2014/0266604 | A1 | 9/2014 | Masood et al. | |
| 2014/0270383 | A1 | 9/2014 | Pederson | |
| 2014/0278629 | A1 | 9/2014 | Stephenson et al. | |
| 2014/0307926 | A1* | 10/2014 | Murakami | G06T 7/20 |
| | | | | 382/107 |
| 2014/0339430 | A1 | 11/2014 | Hillis et al. | |
| 2015/0028993 | A1 | 1/2015 | Dyk et al. | |
| 2015/0193507 | A1* | 7/2015 | Rappoport | G06F 16/24575 |
| | | | | 382/118 |
| 2015/0193718 | A1* | 7/2015 | Shaburov | G06Q 10/06395 |
| | | | | 705/7.39 |
| 2015/0213304 | A1 | 7/2015 | Passe | |
| 2015/0278585 | A1* | 10/2015 | Laksono | G06V 40/103 |
| | | | | 382/103 |
| 2016/0078279 | A1* | 3/2016 | Pitre | A61B 5/165 |
| | | | | 382/118 |
| 2016/0104175 | A1* | 4/2016 | Fanourgiakis | G06Q 10/0637 |
| | | | | 705/7.29 |
| 2016/0110591 | A1* | 4/2016 | Smith | G06V 20/52 |
| | | | | 382/103 |
| 2016/0150124 | A1 | 5/2016 | Panda et al. | |
| 2016/0170998 | A1* | 6/2016 | Frank | G06F 16/337 |
| | | | | 707/748 |
| 2016/0189149 | A1* | 6/2016 | MacLaurin | G06Q 20/40145 |
| | | | | 705/44 |
| 2016/0196728 | A1 | 7/2016 | Suman et al. | |
| 2016/0203699 | A1 | 7/2016 | Mulhern et al. | |

(56) References Cited

U.S. PATENT DOCUMENTS

| | | |
|---|---|---|
| 2016/0217345 A1 | 7/2016 | Appel et al. |
| 2016/0267760 A1 | 9/2016 | Trani |
| 2016/0302711 A1* | 10/2016 | Frank .................. G06F 21/6245 |
| 2016/0330217 A1* | 11/2016 | Gates .................. H04L 63/1441 |
| 2016/0335870 A1 | 11/2016 | Yum |
| 2016/0379046 A1 | 12/2016 | Crandall et al. |
| 2016/0379145 A1 | 12/2016 | Valentino, III et al. |
| 2017/0046496 A1* | 2/2017 | Johnstone ........... G06F 16/2228 |
| 2017/0046566 A1* | 2/2017 | Smith ................. G06K 9/00302 |
| 2017/0061202 A1 | 3/2017 | Shreve et al. |
| 2017/0083757 A1* | 3/2017 | Enomoto ............. G06V 40/176 |
| 2017/0169284 A1 | 6/2017 | Chu et al. |
| 2017/0192994 A1* | 7/2017 | Hong .................... G06F 16/164 |
| 2017/0236029 A1 | 8/2017 | Howell |
| 2017/0236397 A1 | 8/2017 | Myslenski et al. |
| 2017/0255880 A1 | 9/2017 | Daher et al. |
| 2017/0280100 A1 | 9/2017 | Hodge |
| 2017/0294063 A1 | 10/2017 | Hodge |
| 2017/0311863 A1* | 11/2017 | Matsunaga ............ A61B 5/163 |
| 2017/0351909 A1 | 12/2017 | Kaehler |
| 2017/0357846 A1* | 12/2017 | Dey ...................... G06K 9/0061 |
| 2018/0047230 A1 | 2/2018 | Nye |
| 2018/0060157 A1* | 3/2018 | Packham ............ G06F 11/0769 |
| 2018/0069975 A1 | 3/2018 | Honda et al. |
| 2018/0108192 A1 | 4/2018 | Ho et al. |
| 2018/0114238 A1* | 4/2018 | Treiser .................... G06F 16/88 |
| 2018/0124242 A1* | 5/2018 | Zimmerman .......... G06F 40/35 |
| 2018/0154260 A1* | 6/2018 | Sawaki .................. A63F 13/211 |
| 2018/0184959 A1* | 7/2018 | Takahashi .............. G16H 40/67 |
| 2018/0300557 A1* | 10/2018 | Rodenas ................. G11B 27/10 |
| 2018/0308130 A1 | 10/2018 | Hafeez et al. |
| 2018/0336575 A1* | 11/2018 | Hwang .............. G06Q 30/0201 |
| 2019/0005841 A1* | 1/2019 | Loi .......................... H04L 51/22 |
| 2019/0043207 A1 | 2/2019 | Carranza et al. |
| 2019/0059725 A1 | 2/2019 | Greiner |
| 2019/0069311 A1 | 2/2019 | Pallas et al. |
| 2019/0073885 A1 | 3/2019 | Bess et al. |
| 2019/0080274 A1 | 3/2019 | Kovach et al. |
| 2019/0110727 A1* | 4/2019 | Egi ....................... G06F 16/337 |
| 2019/0147676 A1 | 5/2019 | Madzhunkov et al. |
| 2019/0239795 A1* | 8/2019 | Kotake ................. A61B 5/7267 |
| 2019/0279445 A1 | 9/2019 | Gallagher et al. |
| 2020/0005416 A1 | 1/2020 | Wade |
| 2020/0074156 A1* | 3/2020 | Janumpally .......... G06V 40/172 |
| 2020/0082438 A1 | 3/2020 | Tunstall |
| 2020/0125838 A1 | 4/2020 | Dalley, Jr. et al. |
| 2020/0256113 A1 | 8/2020 | Salter et al. |
| 2020/0302187 A1 | 9/2020 | Wang et al. |
| 2020/0302715 A1 | 9/2020 | Tulsidas |
| 2020/0334344 A1 | 10/2020 | Schwartz et al. |
| 2020/0344238 A1 | 10/2020 | Ainsworth et al. |
| 2021/0042527 A1 | 2/2021 | Ton-That |
| 2021/0182542 A1* | 6/2021 | Lau ...................... G06Q 20/202 |
| 2021/0185276 A1* | 6/2021 | Peters ..................... H04N 7/152 |
| 2021/0196169 A1* | 7/2021 | Ainsworth .......... G06K 9/00288 |
| 2021/0201269 A1* | 7/2021 | Ainsworth ............ H04W 4/023 |
| 2021/0202067 A1* | 7/2021 | Williams ............... G16H 20/70 |
| 2021/0223869 A1* | 7/2021 | Heraz .................... G06F 40/30 |
| 2021/0248541 A1* | 8/2021 | Heier .............. G06Q 10/063116 |
| 2021/0298157 A1 | 9/2021 | Olaleye et al. |
| 2021/0374391 A1* | 12/2021 | Jorasch ................. G06V 40/19 |
| 2021/0374426 A1 | 12/2021 | Park et al. |
| 2022/0207915 A1 | 6/2022 | Voss |
| 2022/0329589 A1 | 10/2022 | Buscemi et al. |

FOREIGN PATENT DOCUMENTS

| | | | | |
|---|---|---|---|---|
| DE | 102016000091 A1 | * | 7/2017 | |
| JP | 2017033244 A | * | 2/2017 | |
| JP | 2017073107 A | * | 4/2017 | ............... A61B 5/16 |
| JP | 2018138155 A | * | 9/2018 | |
| JP | 6752819 B2 | * | 9/2020 | ......... G06K 9/00221 |
| WO | WO-2013166341 A1 | * | 11/2013 | ............. A61B 5/004 |
| WO | WO 2016128842 | | 8/2016 | |
| WO | WO-2018096294 A1 | * | 5/2018 | |

OTHER PUBLICATIONS

R. S. Sidhu and M. Sharad, "Smart surveillance system for detecting interpersonal crime," 2016 International Conference on Communication and Signal Processing (ICCSP), 2016, pp. 2003-2007, doi: 10.1109/ICCSP.2016.7754524. (Year: 2016).*

S. Mora, V. Rivera-Pelayo and L. Müller, "Supporting mood awareness in collaborative settings," 7th International Conference on Collaborative Computing: Networking, Applications and Worksharing (CollaborateCom), 2011, pp. 268-277, doi: 10.4108/icst. collaboratecom.2011.247091. (Year: 2011).*

M. Mumtaz and H. Habib, Evaluation of Activity Recognition Algorithms for Employee Performance Monitoring. Pakistan, 2012. (Year: 2012).*

H. Gunes, B. Schuller, M. Pantic and R. Cowie, "Emotion representation, analysis and synthesis in continuous space: A survey," 2011 IEEE International Conference on Automatic Face & Gesture Recognition (FG), Santa Barbara, CA, USA, 2011, pp. 827-834, doi: 10.1109/FG.2011.5771357. (Year: 2011).*

Real-Time Optimization of Employee Productivity using Workplace Mood Analysis An IP.com Prior Art Database Technical Disclosure Authors et al.: Disclosed Anonymously, IP.com No. IPCOM000245225D IP.com Electronic Publication Date: Feb. 18, 2016 (Year: 2016).*

Seddigh A, Berntson E, Platts LG, Westerlund H. Does Personality Have a Different Impact on Self-Rated Distraction, Job Satisfaction, and Job Performance in Different Office Types? PLoS One. May 25, 2016;11(5):e0155295. doi: 10.1371/journal.pone.0155295. PMID: 27223898; PMCID: PMC4880328 (Year: 2016).*

International Preliminary Report on Patentability, mailed on May 14, 2020, from International Application No. PCT/US2018/058971, filed on Nov. 2, 2018. 7 pages.

International Preliminary Report on Patentability, mailed on May 14, 2020, from International Application No. PCT/US2018/058976, filed on Novemember 2, 2018. 8 pages.

International Preliminary Report on Patentability, mailed on May 14, 2020, from International Application No. PCT/US2018/058984, filed on Nov. 2, 2018. 9 pages.

International Preliminary Report on Patentability, mailed on May 14, 2020, from International Application No. PCT/US2018/058996, filed on Nov. 2, 2018. 9 pages.

International Search Report and Written Opinion of the International Searching Authority, mailed on Dec. 21, 2018, from International Application No. PCT/US2018/058971, filed on Nov. 2, 2018. 8 pages.

International Search Report and Written Opinion of the International Searching Authority, mailed on Jan. 4, 2019, from International Application No. PCT/US2018/058971, filed on Nov. 2, 2018. 13 pages.

International Search Report and Written Opinion of the International Searching Authority, mailed on Dec. 21, 2018, from International Application No. PCT/US2018/058984, filed on Nov. 2, 2018. 14 pages.

International Search Report and Written Opinion of the International Searching Authority, mailed on Dec. 21, 2018, from International Application No. PCT/US2018/058996, filed on Nov. 2, 2018. 14 pages.

Turner, A., "Biometrics in Corrections: Current and Future Deployment," Corrections Today, 62-64 (2003).

Miles, A. C., et al., "Tracking Prisoners in Jail with Biometrics: An Experiment in a Navy Brig," NIJ Journal, 253: 1-4 (2006).

Miles, Christopher A. Cohn, Jeffrey P. Tracking Prisoners in Jail With Biometrics: An Experiment in a Navy Brig. National Institute of Justice. (Year: 2006).

Turner, Allan. Biometrics in Corrections: Current and Future Deployment. Corrections Today. (Year: 2003).

* cited by examiner

METHODS AND SYSTEM FOR MONITORING AND ASSESSING EMPLOYEE MOODS

RELATED APPLICATIONS

This application is a § 371 National Phase Application of International Application No. PCT/US2018/058984, tiled on Nov. 2, 2018, now international Publication No. WO 2019/090096 A1, published on May 9, 2019, which International Application claims the benefit under 35 U.S.C. § 119(e) of U.S. Provisional Application No. 62/581,207, filed on Nov. 3, 2017, which is both of which are incorporated herein by reference in their entirety.

BACKGROUND OF THE INVENTION

Enterprises, such as private and public companies, municipal, state and federal governmental agencies, and other entities, will often maintain a number of disparate systems to facilitate their operations, track their business relationships, and maintain security. Employee Resource Management (ERM) systems are computer systems that allow the enterprises to track, schedule, and pay their employees. Access control systems are principally concerned with physical security and the selective access to, restriction of access to, and/or notification of access to the enterprises' buildings and secured parts of those buildings. In addition, other security systems are often employed by the enterprises to round-out their security needs. A common example is a surveillance system.

The ERM systems store and manage many different types of information associated with employees. The ERM system might execute on a single computer system or server, or across multiple computer systems and servers, or be implemented in a cloud-based computer system. The different types of information controlled and managed by the ERM systems include biographic, including demographic, information, payroll and salary information, job performance and attendance information, benefits information, and training and compliance information, to list some common examples.

Modern ERM systems typically combine the functionality of multiple legacy systems that had separately managed and stored the different types of information associated with the employees. These legacy systems might have had separate payroll systems for the payroll and salary information, human resources systems for the biographic, job performance and attendance information, benefits systems for the benefits information, and learning systems for the training and compliance information, in examples. At the same time, the ERM system can simply be a collection of local or remote databases that store the different types of information associated with each employee.

The access control systems typically include access control readers. These readers are often installed at access points of the buildings to control access to restricted areas, such as buildings or areas of the buildings. Examples of access points include front and interior doors of a building, elevators, hallways connecting two areas of a building, to list a few examples. The access control readers authenticate identities of (or authorize) individuals and then permit those authenticated individuals to access the restricted areas through the access points. Typically, individuals interact with the access control readers by swiping keycards or bringing contactless smart cards within range (approximately 2-3 inches or 5 centimeters) of a reader. The access control readers read user information of the keycards, such as credentials of the individuals, and then the access control systems determine if the individuals are authorized to access the restricted areas. If the individuals are authorized to enter the restricted areas, then the access control readers allow access to the restricted areas by unlocking locked doors, signaling that doors should be unlocked, or generating alarms upon unauthorized entry, for example.

More recently, frictionless access control systems are being proposed and designed. These systems typically rely on individuals carrying beacon devices that can broadcast credentials, such as dedicated fob devices or personal mobile computing devices such as tablet or smart phone computing devices. These systems are "frictionless" in that the individual may not have made any overt gesture indicating a desire to access the restricted area, e.g., the individuals did not swipe a keycard. The access control systems will then monitor and track the individuals as they move through the buildings and automatically open access points such as doors when approached, assuming that the individuals are authorized to pass through those access points.

Enterprise surveillance systems are used to help protect people, property, and reduce crime. These systems are used to monitor buildings, lobbies, entries/exits, and secure areas within the buildings of the enterprises, to list a few examples. The surveillance systems also identify illegal activity such as theft or trespassing, in examples. At the same time, these surveillance systems can also have business uses. They can track employee locations across different rooms within buildings and among the different buildings of the enterprises.

In these surveillance systems, surveillance cameras capture image data of scenes. The image data is typically represented as two-dimensional arrays of pixels. The cameras include the image data within streams, and users of the system such as security personnel view the streams on display devices such as video monitors. The image data is also typically stored to a video management system (VMS) for later access and analysis.

SUMMARY OF THE INVENTION

It would be beneficial if the enterprises such as companies or stores or governmental entities could monitor the emotional state of individuals interacting with them, especially as the individuals are entering or leaving, to determine whether the individuals pose potential threats or for less critical uses such as simply whether employees or customers are happy or not.

The proposed security system tracks individuals, obtains emotional state information of the individuals, and determines whether the emotional state information suggests that employees or other individuals pose potential threats at the enterprise. The proposed system can also perform facial recognition to identify and track the individuals. The system can then alert security personnel when the determined emotional states of the individuals indicate fear or anger, and can also restrict access to the building in response. In addition or alternatively, the system can be simply used to collect statistical information on the individuals.

In general, according to one aspect, the invention features an enterprise employee monitoring system. The system might include surveillance cameras and a facial recognition module, an emotional analyzer module and/or an employee database. The surveillance cameras capture image data including employee individuals within the enterprise. The facial recognition module identifies the individuals in the image data, and the emotional analyzer module determines an emotional state of the individuals based upon the image data. The employee database stores employee information and the emotional state information from the emotional analyzer module, based upon the identification performed by the facial recognition module.

The employee monitoring system can additionally generate statistical analysis of the emotional state of the individuals such as employees. Preferably, the statistical analysis is reported to an employee resource management system that maintains the employee database.

In one implementation, employee information is matched to the individuals and/or to groups within the enterprise to determine group level trends in the emotional states of the individuals. In examples, the groups can include institutional groups of the enterprise and social groups. Typically, the system reports the group level trends in the emotional states of the individuals to security guards and/or management personnel and/or human resource managers.

In general, according to another aspect, the invention features an enterprise security system. The security system includes surveillance cameras that capture image data including the individuals within the enterprise, an emotion analyzer for determining an emotional state of the individuals based on the image data, and a security integration system for signaling security guards based on the emotional state determined by the emotion analyzer module.

In general, according to another aspect, the invention features a method of employee monitoring. The method includes capturing image data including individuals within the enterprise, and identifying the individuals in the image data. The method also includes determining an emotional state of the individuals based on the image data, and tracking the emotional state information of the individuals and saving the information to an employee database of an employee resource management system based on the identification of the individuals.

In general, according to yet another aspect, the invention features an enterprise security method. The method includes capturing image data including the individuals within the enterprise, an emotion analyzer module determining an emotional state of the individuals based on the image data, and signaling security guards based on the emotional state determined by the emotion analyzer module.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
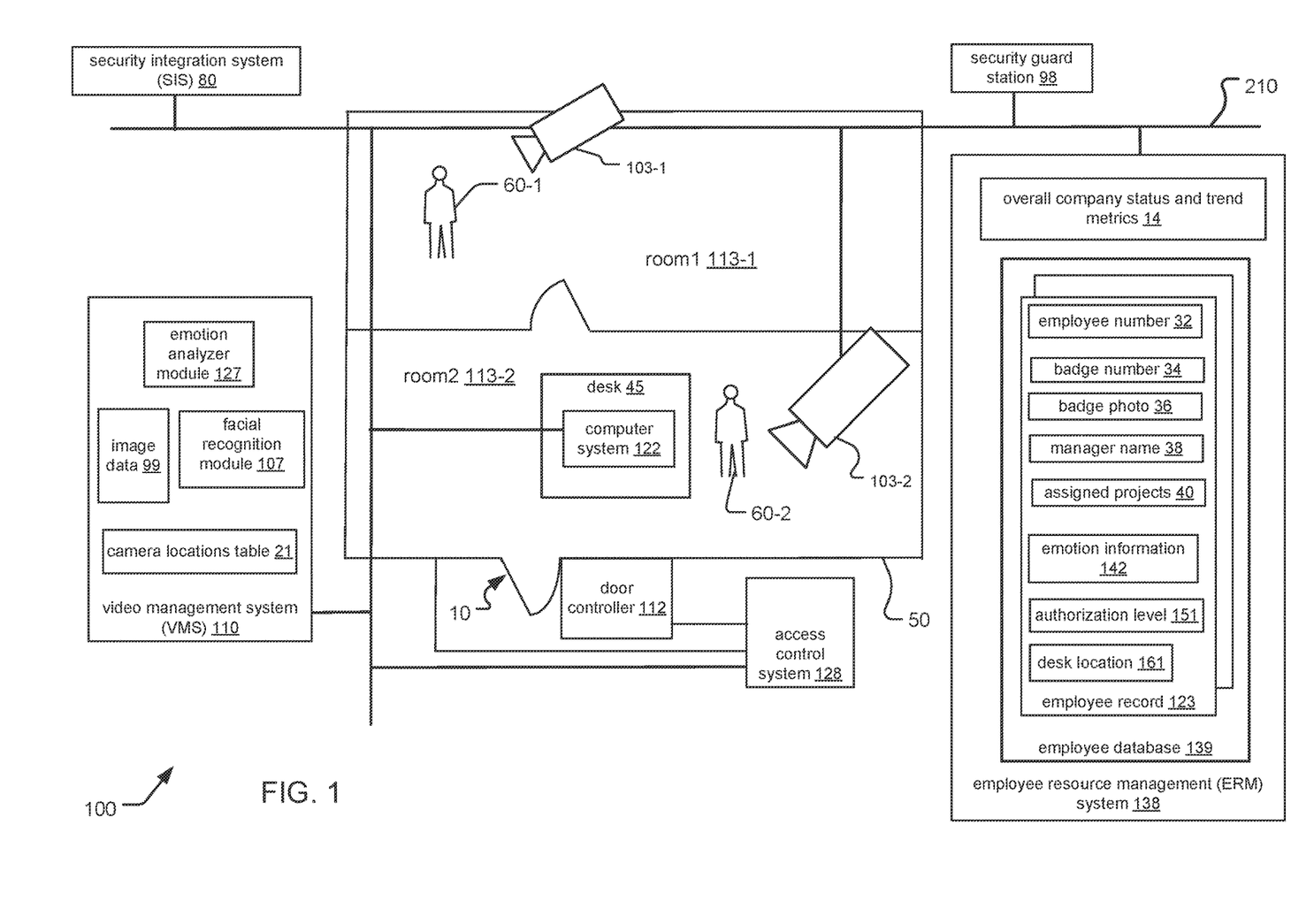
FIG. 1 is a schematic diagram showing an exemplary enterprise including an enterprise security system according to the present invention.

FIG. 1 shows an exemplary enterprise including an enterprise security system 100, which has been constructed according to the principles of the present invention.

The figure shows surveillance cameras 103, client computer systems 122, a security guard station 98, and various other computer systems installed at a building 50 that carry out operations of the enterprise. The other computer systems include an ERM system 138, a VMS 110, and an access control system 128, which are interconnected via a local or enterprise network 210. Finally, a security integration system (SIS) 80 provides some of the important functions of the present invention.

The cameras 103 capture image data 99 of the rooms 113 through the enterprise's building and thus images of individuals 60 in each room 113. Cameras 103-1 and 103-2 are respectively installed in rooms 113-1 and 113-2. The cameras 103 store their image data 99 to the VMS 110. Additionally, in the example of a retail store, additional cameras are positioned to capture images at entrances to the building 50 in which the retail store is located.

The ERM system 138 is preferably as described hereinabove. As such, the ERM system 138 has an employee database 139 that stores employee records 123 of employees 60, and stores overall company status and trend metrics 14. The employee records 123 include information for identifying each employee and locations of desks 45 within the building 50 for the employees. In more detail, each employee record 123 typically includes a name 24, an employee number 32, a badge number 34, a badge photo 36, emotion information 142, an authorization level 151, and one or more desk locations 161. The desk locations 161 list the locations of desks that the employee is authorized to be present at or is otherwise expected to be near during work hours. In addition, the ERM system 138 may also include other information such as databases that store the same information for contractors and visitors to the enterprise.

In the case of the store, the ERM system's database 139 might further include records for customers.

The emotion information 142 includes stored emotional state information for each employee/customer 60. The emotional state information is time-stamped and collected over time.

The VMS 110 stores the image data 99 from the cameras 103 and includes a camera locations table 21, a facial recognition module 107, and an emotion analyzer module 127. The camera locations table 21 typically has a record for each of the surveillance cameras 103. The record contains such information as the room 113 in which the camera 103 is installed. It may also include information concerning the type of camera and possibly even the field of view of the camera with respect to a map or floor layout of the building 50.

The facial recognition module 107 determines facial recognition information of the individuals captured in the image data and monitors movement and/or activity of individuals 60 within the rooms 113. The facial recognition module 107 determines facial recognition information of the individuals captured in the image data and monitors movement and/or activity of individuals 60 within the rooms 113.

The emotion analyzer module 127 determines an emotional state for the individuals/employees 60 from their images in the image data 99. Examples of these emotional states include anger, fear, and happiness, in examples. The emotional analyzer preferably also generates an emotion level, which could simply be a value between 1 and 10. For example, for each individual in the image data, the analyzer module 127 generates a state, such as happy, and the level for that state. For example, "happy, 5" for an individual would indicate an individual that was happier than an individual with "happy, 3".

The access control system 128 controls physical access to access points 10 of the building 50. In the illustrated example, the access points are doors, but may also include hallways or elevators or floors within the buildings of the enterprise. Typically, the access control system 128 further includes card readers for reading employee badges and/or frictionless readers that might validate employees based on credentials provided by a mobile computing device such as a smart phone. In this way, the access control system 128 is able to monitor movement of individuals through access points.

The VMS can be seeded with information concerning the enterprises employees and possibly customer or other individuals that interact with the enterprise. For example, when the individuals 60 individuals are originally hired as employees, a security operator/guard or human resources representative would create the employee record 123 for each employee in the employee database 139. The security guard also takes a picture of the employee's face to use as the badge photo 36, and uses the facial recognition module 107 of the VMS 110 to create stored facial recognition information for each of the employees. The security guard might also create a baseline instance of emotional state information for the employee, using the emotional analyzer module 127.

In the case of the store, the customers might go through a similar registration process or the system would simply track repeat customers via a customer number for example. Customers could be identified by name or only using a customer number. Repeat customers and the emotional state of those customers would be tracked over the visits to the store.

The facial recognition information created and stored by the facial recognition module 107 can be of different types. In one example, the information is a biometric identifier such as a facial signature of the individual. In another example, the information is simply a still image of the person's face extracted from the image data, also known as a facial patch.

The facial signature for an individual is a unique value or set of values that represent the face of an individual/employee/customer. The facial recognition module 107 uses one or various predetermined facial signature algorithms to create the facial signature, based upon various features of each person's face. These features include the eyes, nose, mouth, eyebrows, cheekbones, and chin of each face, and distances between each of these features, in examples.

The facial recognition module also maps each instance of facial recognition information (e.g. the facial signature or facial patch) for each employee to a user credential or other identifier (OD). In this way, the OD associated with each instance of stored facial recognition information can be used to identify the individual for which the facial signature was obtained.

The VMS 110 then stores the facial recognition information and associated ID for identifying each employee or customer. In one example, the VMS stores this information locally to the VMS 110. In another example, the VMS 110 might store this information to the employee or customer record 123 for each employee or customer.

The VMS also stores the obtained emotional state information to the emotion information 114 in the employee/customer record 123 for each employee/customer 60.

The enterprise security or monitoring system 100 generally operates as follows.

The cameras 103 also capture and send the image data 99 of the individuals to the VMS 110. The VMS 110 then stores the image data 99, performs facial recognition upon the image data 99 to identify the individuals 60, and determines an emotional state of the individuals based upon the image data 99.

From this analysis, the VMS 110 generates a meta data stream. The meta data stream includes an indication of each individual detected in the image data from the various security cameras, a time stamp of the time of detection, a location of the individual obtained by reference to the camera locations table 21, an identification of the individual such as employee or customer number, if the facial recognition module was able to identify the individual, a detected emotional state of the individual, and the determined level for that state.

The ERM system 138 receives surveillance meta data stream including the time-stamped emotional state information sent from the VMS 110, and stores the information to the employee records 123 for each individual to the employee database 139 and/or a customer database as appropriate.

The security integration system (SIS) 80 functions to integrate the operation of VMS 110 with the ERM system 138 and handle security issues. The SIS 80 can take many different forms. As such, the SIS 80 can be a separate computer system or could be a process that executes on a computer associated with the VMS 110 or the ER or even a separate computer system or a computer system integrated with the ERM computer systems.

The SIS 80 receives the surveillance meta data stream from the VMS 110, uses the IDs of the identified/tracked individuals in the stream to identify the individuals, and can perform different operations based upon the emotional state information associated with each individual in the stream. In one example, if the emotional state information indicates that an individual is very upset or angry, the SIS 80 can signal security guards to this effect. In another example, the SIS 80 obtains the associated employee records 123 for the individuals 60, and performs statistical analysis on the information. In yet another example, the SIS 80 can obtain employee records for other employees having the same institutional information or social information as "upset" individuals. The SIS 80 can then determine trends in the emotional states of the employees at a group level. Examples of these groups include institutional groups (e.g. employees having the same manager, assigned project, or building location) and social groups (e.g. employees having the same professional and/or professed political affiliations and outside work interests).

Figure 2:
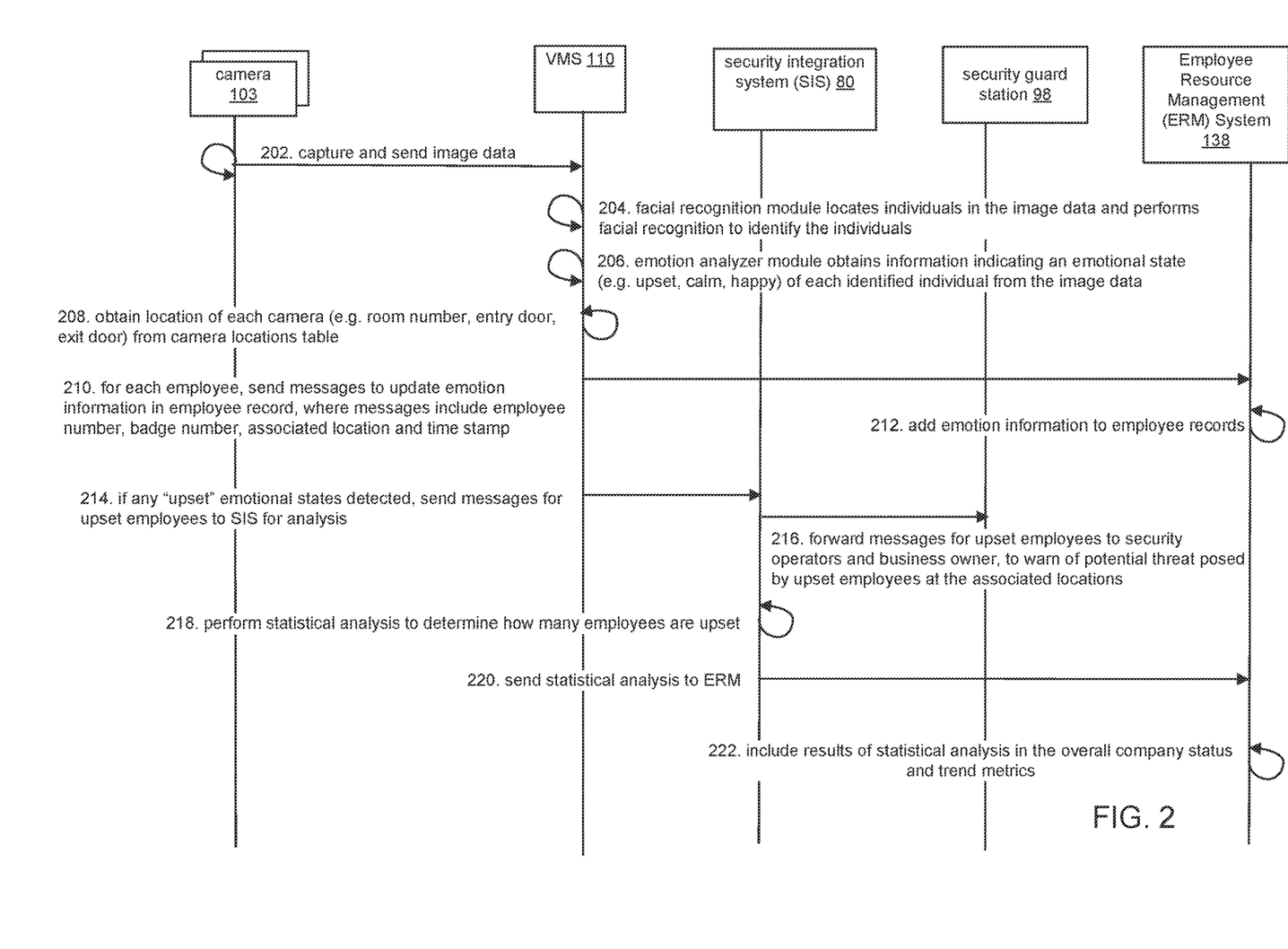
FIG. 2 is a sequence diagram showing operation of the enterprise security system when deployed as an employee monitoring system.

FIG. 2 is a sequence diagram that illustrates a method of operation of the enterprise security monitoring system.

In step 202, the cameras 103-1 and 103-2 within the rooms 113-1 and 113-2 of the building 50 capture the image data 99 of scenes in the rooms 113. The cameras 103 send the image 99 to the VMS 110 for storage and subsequent analysis.

In step 204, the facial recognition module 107 of the VMS 110 locates the individuals 60 in the image data 99 and performs facial recognition of the individuals to identify the individuals 60. For this purpose, the facial recognition module 107 preferably uses the same facial recognition algorithms used when the security guards first registered the individuals as employees.

According to step 206, the emotion analyzer module 127 obtains information indicating an emotional state (e.g. upset/angry, calm, fear) and emotion level of each identified individual from the image data 99. In step 208, the VMS 110 obtains the location of each camera (e.g. room number, entry door, exit door) from the camera locations table 21.

It can also be appreciated that the facial recognition module 107 and the emotion analyzer module 127 can be included within and execute upon other components of the enterprise security monitoring system and/or the enterprise security system. In one example, the facial recognition module 107 and the emotion analyzer module 127 might be integrated within the cameras 103 and execute upon a microcontroller of the cameras 103. In other examples, these components might execute upon a microcontroller or central processing unit (CPU) of the ACS 128 or be located in a computer system that is remote to the enterprise, such as a cloud system. In yet another example, the facial recognition module 107 and the emotion analyzer module 127 could be located in different components.

In step 210, the VMS 110 sends a meta data stream to the ERM system 138, and to the SIS 80 in step 214. Specifically, for each employee and/or possibly customer, the VMS 110 sends messages to update the emotion information 142 including state and level in the employee or customer record 123 for each identified employee/customer/individual in the stream. The messages/streams include the emotion information (state/level), the employee/customer number 32, badge number 34, associated location and time stamp, in examples. The ERM system 138 adds the emotion information 142 to the employee/customer records 123 in step 212.

The SIS 80 receives the meta data stream from the VMS in step 216. The SIS then forwards messages for the upset employees and/or customers and/or other individuals to security guards and possibly the business owner, to warn of potential threat posed by upset employees at the associated locations, especially in the case where the levels of emotion are high, such as 9 or 10.

In step 218, the SIS 80 also performs statistical analysis to determine how many employees are upset, and sends the statistical analysis to ERM system 138 in step 220. Then, in step 222, the ERM system 138 includes the results of the statistical analysis in its overall company status and trend metrics 14.

Figure 3:
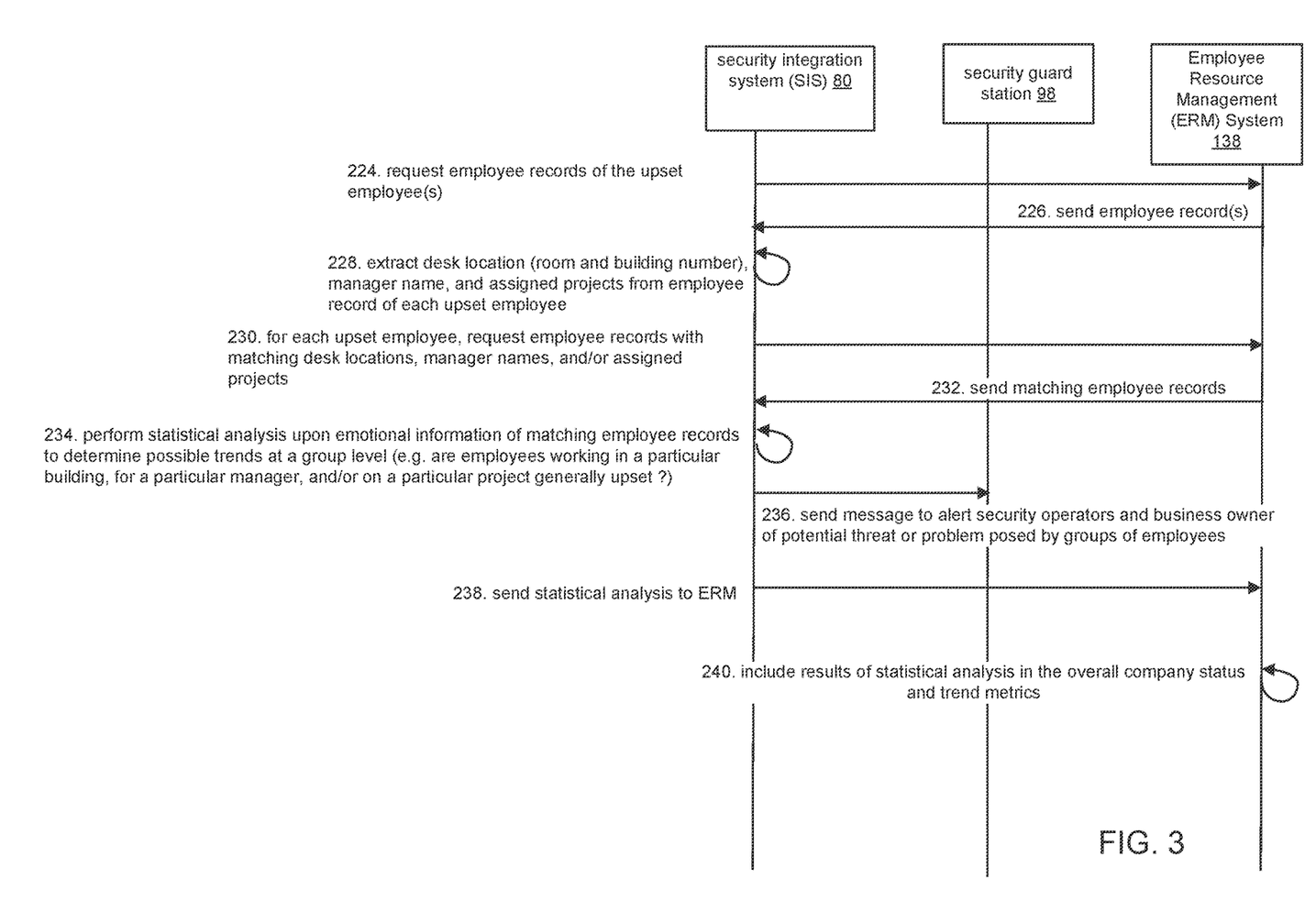
FIG. 3 is a sequence diagram showing an additional operation of the monitoring system, based upon emotional state information of the individuals determined in FIG. 2.

FIG. 3 shows additional operations that the SIS 80 can perform, based upon the emotional state information received in FIG. 2 when functioning as an enterprise employee monitoring system.

In step 224, the SIS 80 requests the employee records 123 of the upset employee(s) previously determined in FIG. 2. The SIS 80 requests the employee records from the ERM system 138 including the groups such as working group or division or section of the enterprise, and the ERM system returns the records in step 226.

In step 228, the SIS 80 extracts the desk location (room and building number), manager name, formal and/or informal and/or social group, and assigned projects from the employee records 123 of each upset employee 60.

Then, for each upset employee, the SIS 80 request employee records 123 for other employees with matching desk locations, manager names, and/or assigned projects and/or other group, from the ERM system 138 in step 230. The ERM system sends the matching employee records 123 in step 232.

According to step 234, the SIS 80 performs statistical analysis upon the emotion information 14 of the matching employee records to determine possible trends at the group level. In this way, a security guard or human resources person might be able to infer that employees working in a particular building, for a particular manager, and/or on a particular project are generally upset, in examples.

In step 236, the SIS 80 sends a message to alert security guards and possibly business owners of the potential threat or problem posed by the groups of employees. The SIS also sends the statistical analysis to ERM system 138 in step 238.

According to step 240, the ERM system 138 includes the results of the statistical analysis in its overall company status and trend metrics 14.

Figure 4:
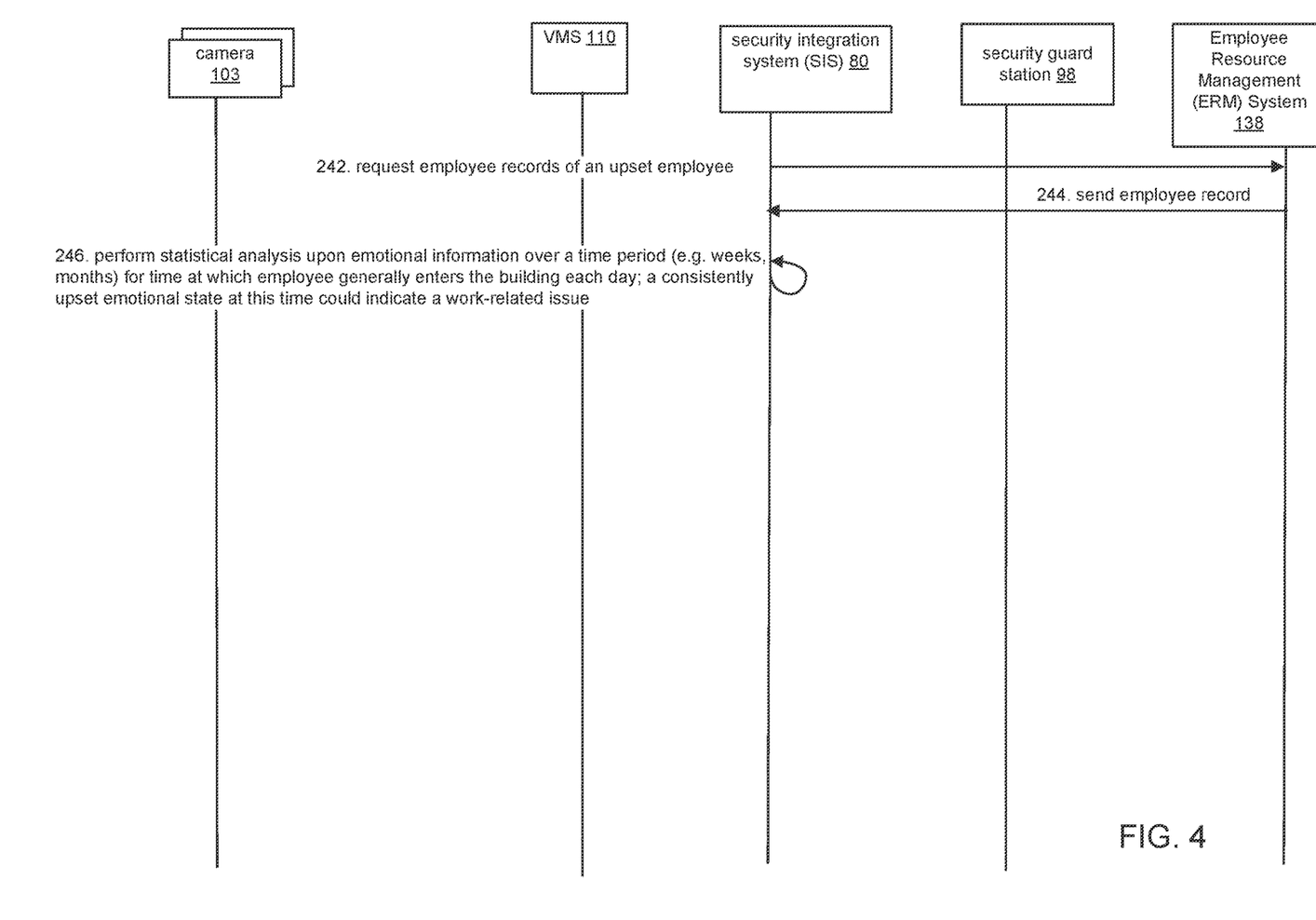
FIG. 4 is a sequence diagram showing yet another operation of the monitoring system, based upon emotional state information of the individuals determined in FIG. 2.

FIG. 4 also shows additional operations that the SIS 80 can perform, based upon the employee emotional state information received in FIG. 2.

In step 242, the SIS 80 requests the employee records 123 of an "upset" employee 60 (i.e. an employee that the emotion analyzer module 127 determined to have an upset or fearful emotional state). The ERM system 138 sends the employee record 123 in step 244.

The SIS 80, in step 246, then perform statistical analysis upon the emotional information over a time period (e.g. weeks, months), for a time at which employee generally enters the building 50 each day, in one example. In this way, a consistently upset emotional state at this time for the employee 60 could indicate a work-related issue that requires further investigation by human resources personnel, in one example.

In another example, if an employee 60 is determined to be consistently in an upset emotional state when leaving work each day, then there may be an issue outside of work affecting that employee 60. Such information can be used to determine potential threats posed by the employees 60 before they manifest into actual threats, either in the workplace or outside of the workplace, in examples.

In yet another example, if an employee 60 is determined to have a sudden change in their emotional state as compared to their stored emotion information 14 over time, this could also be indicative of an employee issue that requires follow-up by human resources personnel.

The above information can be used to determine potential threats posed by the employees 60 before they manifest into actual threats, either in the workplace or outside of the workplace, in examples.

It can also be appreciated that cameras 103 located throughout the buildings of an enterprise can capture the emotional states of the individuals 60 as they work and interact with others. In this way, based on the facial recognition information of manager and worker employees and their emotional state information, the SIS 80 could compile statistical information on interactions between groups of manager and worker employees over time to determine whether there are any personnel issues that require additional investigation by human resources personnel.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system, comprising:
    surveillance cameras configured to capture image data of a scene within an enterprise, the scene including an individual; and
    a device comprising:
        a memory storing instructions thereon; and
        at least one processor coupled with the memory and configured by the instructions to:
            determine, based on the image data, emotional state information defining an emotional state of the individual;
            determine, based on the image data and the emotional state information, an emotion level for the individual corresponding to the emotional state information of the individual, the emotion level quantifying the emotional state according to a defined scale, wherein the defined scale discretizes a range of intensity of a type of the emotional state;
            determine individual information based on the image data in response to the emotional state information corresponding to a particular type of the emotional state; and
            send, to a second device, the emotional state information, the emotion level, the individual information, and a desk location of a desk of the individual within a building of the enterprise in response to the emotion level for the individual achieving a predefined threshold level in the defined scale, wherein the predefined threshold level exceeds a lower limit of the range of intensity,
        wherein the second device is configured to:
            request records for other individuals with matching desk locations of the desk location of the individual within the building of the enterprise; and
            perform statistical analysis of the emotional state information and the emotion level of the individual and of the other individuals to detect a group level trend in an emotional state of a group including the individual and the other individuals.

2. The system of claim 1, wherein the emotional state information is determined over time and time-stamped, and wherein the at least one processor is further configured by the instructions to generate statistical analysis, over a defined time interval, of the emotional state information of the individual at a defined time of day.

3. The system of claim 2, wherein the at least one processor is further configured by the instructions to report the statistical analysis to a second system.

4. The system of claim 1, wherein the at least one processor is further configured by the instructions to report the group level trend in the emotional state of the group to a security personnel device.

5. The system of claim 1, wherein the individual information includes at least one of name of the individual or employee identifier of the individual.

6. The system of claim 1, wherein the particular type of the emotional state includes at least one of angry, upset, or fearful.

7. A non-transitory computer-readable device having instructions thereon that, when executed by at least one computing device, causes the at least one computing device to perform operations comprising:
    capturing image data of a scene within an enterprise, the scene including an individual;
    determining, based on the image data, emotional state information defining an emotional state of the individual;
    determining, based on the image data and the emotional state information, an emotion level for the individual corresponding to the emotional state information, the emotion level quantifying the emotional state according to a defined scale, wherein the defined scale discretizes a range of intensity of a type of the emotional state;
    determining individual information based on the image data in response to the emotional state information corresponding to a particular type of the emotional state; and
    sending, to a second computing device, the emotional state information, the emotion level, the individual information, and a desk location of a desk of the individual within a building of the enterprise in response to the emotion level for the individual achieving a predefined threshold level in the defined scale, wherein the predefined threshold level exceeds a lower limit of the range of intensity, wherein the second computing device is configured to:

request records for other individuals with matching desk locations of the desk location of the individual within the building of the enterprise; and perform statistical analysis of the emotional state information and the emotion level of the individual and of the other individuals to detect a group level trend in an emotional state of a group including the individual and the other individuals.

8. A method, comprising:

capturing image data of a scene within an enterprise, the scene including an individual;

identifying the individual in the image data;

determining, based on the image data, an emotional state information of the individual defining an emotional state of the individual;

determining, based on the image data and the emotional state information, an emotion level for the individual for the emotional state information, the emotion level quantifying the emotional state according to a defined scale, wherein the defined scale discretizes a range of intensity of a type of the emotional state;

determining individual information based on the image data in response to the emotional state information corresponding to a particular type of the emotional state; and sending, to a remote device, the emotional state information, the emotion level, the individual information, and a desk location of a desk of the individual within a building of the enterprise in response to the emotion level for the individual achieving a predefined threshold level in the defined scale, wherein the predefined threshold level exceeds a lower limit of the range of intensity, wherein the remote device is configured to:

request records for other individuals with matching desk locations of the desk location of the individual within the building of the enterprise; and perform statistical analysis of the emotional state information and the emotion level of the individual and of the other individuals to detect a group level trend in an emotional state of a group including the individual and the other individuals.

9. The method of claim 8, wherein the emotional state information is determined over time and time-stamped, the method further comprising generating statistical analysis, over a defined time interval, of the emotional state of the individual at a defined time of day.

10. The method of claim 9, further comprising reporting the statistical analysis to an employee resource management system.

11. The method of claim 8, further comprising reporting the group level trend to a remote device.

12. The method of claim 8, further comprising identifying, based on the group level trend, a personnel issue for investigation.

13. The method of claim 8, further comprising alerting, based on the group level trend, at least one of security guards or owners of the enterprise of potential threats or problems.

14. The method of claim 8, further comprising restricting access to a premises of the enterprise in response to the emotional state information corresponding to the particular type of the emotional state.

15. The method of claim 10, wherein the remote device is configured to request, from the employee resource management system, the other individuals with the matching desk locations of the desk location of the individual.

* * * * *